United States Patent [19]

Distler et al.

[11] 4,113,764

[45] * Sep. 12, 1978

[54] MANUFACTURE OF N-SUBSTITUTED GLYCINONITRILES

[75] Inventors: Harry Distler, Bobenheim; Helmut Schlecht; Erwin Hartert, both of Ludwigshafen, all of Fed. Rep. of Germany

[73] Assignee: BASF Aktiengesellschaft, Ludwigshafen, Fed. Rep. of Germany

[*] Notice: The portion of the term of this patent subsequent to May 10, 1994, has been disclaimed.

[21] Appl. No.: 743,517

[22] Filed: Nov. 19, 1976

[30] Foreign Application Priority Data

Dec. 11, 1975 [DE] Fed. Rep. of Germany ....... 2555769

[51] Int. Cl.$^2$ .................. C07C 120/00; C07C 120/02
[52] U.S. Cl. .............................. 260/465.5 A; 562/575
[58] Field of Search ................................. 260/465.5 A

[56] References Cited

U.S. PATENT DOCUMENTS

| | | | |
|---|---|---|---|
| 2,860,164 | 11/1958 | Kroll et al. | 260/465.5 A X |
| 3,409,666 | 11/1968 | Foreman | 260/465.5 A X |
| 3,415,878 | 12/1968 | Gaunt | 260/465.5 A X |
| 3,463,811 | 8/1969 | Godfrey et al. | 260/465.5 A X |
| 3,499,920 | 3/1970 | Daniels | 260/465.5 A |
| 4,022,815 | 5/1977 | Schlecht et al. | 260/465.5 A |

FOREIGN PATENT DOCUMENTS 656,350  2/1938  Fed. Rep. of Germany ... 260/465.5 A

*Primary Examiner*—Joseph Paul Brust
*Attorney, Agent, or Firm*—Keil, Thompson & Shurtleff

[57] ABSTRACT

N-Alkylglycinonitriles are manufactured by reacting N-alkylamines with formaldehyde and hydrocyanic acid under specific reaction conditions in respect of temperature, reaction time and hydrocyanic acid concentration. The products are starting materials for the manufacture of dyes, fungicides, bactericides, textile assistants and assistants used in dental cosmetics, gas purification and waterproofing.

9 Claims, No Drawings

MANUFACTURE OF N-SUBSTITUTED GLYCINONITRILES

The present invention relates to a process for the manufacture of N-substituted glycinonitriles by reacting N-substituted amines with formaldehyde and hydrocyanic acid under specific reaction conditions in respect of temperature, reaction time and hydrocyanic acid concentration.

German Pat. No. 656,350 discloses that glycollic acid nitrile can be reacted with an excess of methylamine in aqueous solution under pressure, to give sarcosinonitrile. To achieve good yields of sarcosinonitrile, an excess of up to 10 moles of methylamine per mole of hydroxyacetonitrile is recommended (German Pat. No. 656,350). If stoichiometric amounts are used, substantial amounts of the nitrile of methyldiglycolamic acid are formed, and this compound is difficult to remove.

Another method for the manufacture of N-substituted glycinonitriles uses formaldehyde, in the presence of sodium bisulfite compounds, as the starting material, the aldehyde being reacted with sodium cyanide and aliphatic amines. The method using sodium cyanide and sodium bisulfite, if carried out industrially, presents problems of pollution of the environment as a result of alkali metal salts, which can contain residual cyanides, being formed as by-products. The use of the amines, employed in this reaction, in the form of salts, e.g. chlorides, has also been disclosed (Jean Mathieu and Jean Weil-Raynal, Formation of C — C - Bonds, Vol. I, pages 442 – 446 (Georg Thieme Verlag Stuttgart 1973)).

All these processes are unsatisfactory from the point of view of simple and economical operation, good yield of end product and ease of working up, particularly as regards protection of the environment and purification of effluents.

The present invention relates to a new process for the simpler and more economical manufacture of N-alkyl-glycinonitriles.

Our U.S. Application Ser. No. 649,582, filed Jan. 16, 1976, now U.S. Pat. No. 4,022,815, relates to a process for the manufacture of N-substituted glycinonitriles of the formula

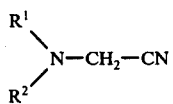

where $R^1$ and $R^2$ are identical or different and each is an aliphatic radical, and $R^2$ may also be hydrogen, by reacting formaldehyde with an amine and a cyano compound, in which process an N-substituted amine of the formula

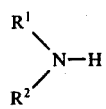

where $R^1$ and $R^2$ have the above meanings, is reacted with formaldehyde and hydrocyanic acid in the presence of water for from 0.1 to 4 hours at from 0° to 40° C, the concentration of the hydrocyanic acid during the reaction being not more than 0.1 percent by weight, based on the reaction mixture.

We have found that the process of the said application can be further improved by carrying out the reaction at from above 40° up to 80° C.

Where dimethylamine is used, the reaction can be represented by the following equations:

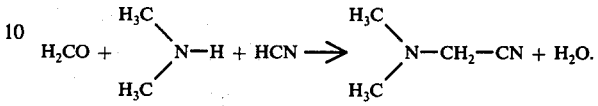

Compared to conventional processes, the process of the invention gives N-substituted glycinonitriles more simply and more economically, and in better yield and higher purity. The process is particularly suitable for industrial continuous operation, presents no essential problems with regard to effluent and produces less pollution of the environment. By-products, e.g. nitriles of alkyldiglycolamic acids or methylolamines resulting from the presence of formaldehyde, are not formed to a significant degree. All these advantageous properties are surprising in the light of the art.

Formaldehyde may be employed as a liquid or a gas, but is in general employed as an aqueous solution, advantageously of from 10 to 50 percent strength by weight and preferably of from 30 to 40 percent strength by weight. Hydrocyanic acid may be used as a gas or, advantageously, as a liquid or in aqueous solution. The amine starting material II may be employed as such or, advantageously, in solution, preferably in aqueous solution; the use of solutions of from 40 to 60 percent strength by weight is advantageous. The three starting materials may be reacted in stoichiometric amounts, or alternatively any one of the components may be employed in excess, preferably in an amount of from 0.1 to 2 moles of amine and/or of from 0.01 to 0.1 mole of hydrocyanic acid per mole of formaldehyde (taken as 100% strength). Preferred starting materials II and, accordingly, preferred end products I are those where $R^1$ and $R^2$ are identical or different and each is alkyl of 1 to 20, preferably 1 to 8, and especially 1 to 4, carbon atoms or alkenyl of 2 to 20, preferably 2 to 8, carbon atoms, and $R^2$ may also be hydrogen. The above radicals may in addition be substituted by groups which are inert under the reaction conditions, e.g. alkyl or alkoxy each of 1 to 4 carbon atoms.

Examples of suitable starting materials II are: methylamine, ethylamine, n-propylamine, isopropylamine, n-butylamine, isobutylamine, sec.-butylamine, tert.-butylamine, pentylamine, pentyl-(2)-amine, pentyl-(3)-amine, n-hexylamine, n-heptylamine, n-octylamine, n-nonylamine, n-decylamine, n-tridecylamine, n-octadecylamine, oleylamine, 2-ethylhexylamine, 2,2,6-trimethyl-n-pentylamine, 2-ethylpentylamine, 3-ethylpentylamine, 2,3-dimethyl-n-butylamine, 2,2-dimethyl-n-butylamine, 2-methylpentylamine, 3-methylpentylamine, 2,2,4-trimethylpentylamine, 2-methylheptylamine, 3-methylheptylamine, 4-methylheptylamine, 3-ethylhexylamine, 2,2-dimethylhexylamine, 2,3-dimethylhexylamine, 2,4-dimethylhexylamine, 2,5-dimethylhexylamine, 3,3-dimethylhexylamine, 3,4-dimethylhexylamine, 2-methyl-3-ethylpentylamine, 3-methyl-3-ethylpentylamine, 2,2,3-trimethylpentylamine, 2,2,4-trimethylpentylamine, 2,3,3-trimethylpentylamine, 2,3,4-trimethylpentylamine and 2,2,3,3-tetramethylbutylamine, dimethylamine, diethylamine, di-(n-propyl)-amine, diisopropylamine, di-(n-butyl)-amine, diisobutylamine, di-(sec.-butyl)-amine, di-(tert.-butyl)-amine, dipentylamine, di-(pentyl)-(2)-amine, di-(pentyl)-(3)-amine, di-(n-hexyl)-amine, di-(n-heptyl)-amine, di-(n-octyl)-amine, di-(n-nonyl)-amine, di-(n-decyl)-amine, di-(2-ethylhexyl)-amine, di-(2,2,6-trimethyl-n-pentyl)-amine, di-(2-ethylpentyl)-amine, di-(3-ethylpentyl)-amine, di-(2,3-dimethyl-n-butyl)-amine, di-(2,2-dimethyl-n-butyl)-amine, di-(2-methylpentyl)-amine, di-(3-methylpentyl)-amine, di-(2,2,4-trimethylpentyl)-amine, di(2-methylheptyl)-amine, di-(3-methylheptyl)-amine, di-(4-methylheptyl)-amine, di-(3-ethylhexyl)-amine, di-(2,2-dimethylhexyl)-amine, di-(2,3-dimethylhexyl)-amine, di-(2,4-dimethylhexyl)-amine, di-(2,5-dimethylhexyl)-amine, di-(3,3-dimethylhexyl)-amine, di-(3,4-dimethylhexyl)-amine, di-(2-methyl-3-ethylpentyl)-amine, di-(3-methyl-3-ethylpentyl)-amine, di-(2,2,3-trimethylpentyl)-amine, di-(2,2,4-trimethylpentyl)-amine, di-(2,3,3-trimethylpentyl)-amine, di-(2,3,4-trimethylpentyl)-amine and di-(2,2,3,3-tetramethylbutyl)-amine, and corresponding amines which contain 2 of the above radicals which, however, are not identical, e.g. methylethylamine.

The reaction is carried out at from more than 40° up to 80° C, in general at between 40° and 80° C, preferably at from 45° to 75° C and in particular at from 50° to 70° C, under pressure or, preferably, at atmospheric pressure, batchwise or, preferably, continuously. Water is used advantageously in the form of aqueous formaldehyde solution and/or amine solutions, and in addition water is formed in the actual reaction; overall, a total amount of from 1 to 6, preferably from 3 to 4, moles of water, per mole of formaldehyde, is suitable. Hydrocyanic acid is added to the starting mixture before and during the reaction, in an amount such that the concentration during the reaction is not more than 0.1, preferably from 0.01 to 0.1 and especially from 0.05 to 0.1 percent by weight of hydrocyanic acid, based on the reaction mixture. The reaction time (or, in continuous operation, the residence time) is from 0.1 to 4, preferably from 1 to 2, hours. Preferably, water is used as the sole solvent, but organic solvents which are inert under the reaction conditions may also be present. Examples of suitable solvents are aromatic hydrocarbons, e.g. toluene, benzene, ethylbenzene, o-, m- und p-xylene, isopropylbenzene and methylnaphthalene, aliphatic or cycloaliphatic hydrocarbons, e.g. heptane, α-pinene, pinane, nonane, gasoline fractions having a boiling range of from 70° to 190° C, cyclohexane, methylcyclohexane, petroleum ether, decalin, hexane, ligroin, 2,2,4-trimethylpentane, 2,2,3-trimethylpentane, 2,3,3-trimethylpentane and octane, and corresponding mixtures. The solvent is advantageously used in an amount of from 40 to 10,000 percent by weight, preferably from 50 to 1,500 percent by weight, based on starting material II.

The reaction may be carried out as follows: a mixture of formaldehyde, water, hydrocyanic acid and starting amine II, with or without an organic solvent, is kept at the reaction temperature for the duration of the reaction. Some of the hydrocyanic acid is added to the starting mixture, and during the reaction hydrocyanic acid is added in portions or continuously in such a way that the above hydrocyanic acid concentration is maintained throughout the duration of the reaction. The hydrocyanic acid concentration can advantageously be measured continuously by means of a silver-calomel electrode. The end product is then isolated from the reaction mixture by conventional methods, e.g. by distillation or by extraction with, for example, cyclohexane, followed by distillation of the solvent.

In a preferred embodiment, the end product in the reaction mixture is subjected directly, without isolation, to the saponification reaction. The end product I is sapanified by conventional methods, as a rule in an alkaline medium, preferably in aqueous solutions of alkaline earth metal hydroxides or alkali metal hydroxides or, expediently, of alkali metal salts such as sodium carbonate, bicarbonate, acetate or formate or potassium carbonate, bicarbonate, acetate or formate. Sodium hydroxide solution and potassium hydroxide solution are preferred. For example, mixtures, of from 30 to 40 percent strength by weight, of the end product in the above solutions are employed, and the saponification is advantageously carried out at a pH of from 9 to 14 and at from 0° to 150° C, especially at from 45° to 115° C, for from 2 to 30 hours. For example, alkali, alkali metal salts or aqueous solutions of such compounds are added to the mixture, and the end product I is saponified in the mixture, in the above manner. It is advantageous to carry out the saponification with from 1 to 2 equivalents of alkali or alkali metal salt, based on isolated end product I, and with from 1 to 6 equivalents of alkali or alkali metal salt, based on end product I which has not been isolated and is present in the reaction mixture, as described above. In a preferred embodiment, the reaction mixture passes through different, preferably 2 or 3, saponification stages at increasing temperature, e.g. through the stirred kettles of a stirred kettle cascade. A two-stage saponification is preferably carried out at from 55° to 110° C. with a residence time of from 3 to 20 hours, in the first stage (first stirred kettle) and at from 45° to 70° C, with a residence time of from 3 to 10 hours, in the second stage (second stirred kettle); in the case of a three-stage saponification, the conditions are from 55° to 60° C, with a residence time of from 2 to 3 hours, in the first stage, from 90° to 95° C, with a residence time of from 6 to 8 hours, in the second stage, and from 110° to 115° C, with a residence time of from 6 to 8 hours, in the third stage. This stepwise saponification surprisingly avoids discolorations and worsening of the yield. The salt of the N-alkylglycine corresponding to the end product I is then isolated from the saponification mixture by conventional methods, e.g. by evaporation.

The N-substituted glycinonitriles which may be obtained by the process of the invention are valuable starting materials for the manufacture of dyes, fungicides, bactericides, textile assistants, and assistants used in dental cosmetics, gas purification and waterproofing. Regarding the use of the compounds, reference may be made to the above publications and to Ullmanns Encyklopadie der technischen Chemie, volume 8, pages 212 and 213.

In the Examples which follow, parts are by weight.

EXAMPLE 1 a. Per hour, 200 parts of a 30 percent strength by weight aqueous formaldehyde solution, 54 parts of liquid hydrocyanic acid and 214 parts of a 42 percent strength by weight dimethylamine solution are slowly introduced into a stirred kettle at 72° C; during the reaction the hydrocyanic acid concentration does not exceed 0.1 percent by weight, based on the total mixture. The average hydrocyanic acid concentration is from 0.08 to 0.09 percent by weight. The reaction mixture is then distilled. Per hour, 330 parts (98% of theory) of N-dimethylglycinonitrile of boiling point 63° C/41 mm Hg and of $n_D^{20} = 1.4107$ are obtained.

b. The reaction is carried out by the method of Example 1a) but the end product I is not isolated and instead is directly processed further. After a residence time of 2 hours, 464 parts per hour of the reaction mixture are run into the saponification kettle, into which 378 parts per hour of 30 percent strength by weight potassium hydroxide solution are introduced at from 50° to 55° C. After a residence time of 2½ hours, the saponification solution is heated to 90° – 95° C in the first kettle — equipped with a condenser and off-gas outlet — of a cascade. After a residence time of 8 hours, the saponification solution is introduced into a second saponification kettle, equipped with a condenser, where a temperature of from 110° to 115° C is maintained. At the same time, 200 parts of water and 550 parts of steam at 170° C are introduced per hour. 34 parts per hour of gaseous ammonia and 1,000 parts per hour of a 3 percent strength by weight ammonia solution are driven off through a heated column surmounted by a reflux condenser. Per hour, 558 parts of a 42 percent strength by weight aqueous colorless solution of the potassium salt of dimethylglycine are obtained.

EXAMPLE 2 a. Per hour, 400 parts of 30 percent strength by weight formaldehyde, 108 parts of liquid hydrocyanic acid and 458 parts of 40 percent strength by weight methylamine solution are introduced into a stirred kettle at 52° C, following the procedure of Example 1, the hydrocyanic acid concentration in the reaction space being kept below 0.1 percent by weight. After a mean residence time of 30 minutes, the reaction mixture is passed into a reactor which is at 52° C. Here, the cyanide concentration falls to below 500 ppm, based on the total mixture. The average hydrocyanic acid concentration is 0.04 percent by weight. Per hour, 966 parts of a reaction mixture are obtained, from which 270 parts (96.4% of theory) of N-methylglycinonitrile, of boiling point 65° C/20 mm Hg, are obtained per hour, by azeotropic dehydration with toluene.

b. The reaction is carried out by the method of Example (2a) but the end product I is not isolated and instead is directly processed further. After a mean residence time of 1 hour, 966 parts per hour of the reaction mixture are run into a saponification kettle, the method being as described in Example 1, and per hour 200 parts of water and 548 parts of 30 percent strength by weight sodium hydroxide solution at 45° C are introduced into this kettle. After a residence time of 2½ hours, the saponification solution passes into another saponification kettle which is at 100° C. After a mean residence time of 4 hours, the mixture is run into a post-reactor, where the reaction is completed at 110° C, the residence time being 3 hours. Per hour, 1,034 parts of a 38 percent strength by weight sodium sarcosinate solution, of density 1.2, is obtained, ammonia, methylamine and water being evaporated off at the same time.

EXAMPLE 3

Per hour, 292 parts of diethylamine, 108 parts of hydrocyanic acid and 400 parts of a 30 percent strength by weight aqueous formaldehyde solution are introduced into a stirred kettle at 60° C, using the method of Example 1, the hydrocyanic acid concentration being kept below 0.1 percent by weight, based on the total mixture, during the reaction. On average, the hydrocyanic acid concentration is from 0.08 to 0.09 percent by weight. Per hour, 800 parts of material are discharged and separate into two phases. 30 parts of sodium bicarbonate are added, whilst stirring, and the organic phase is separated off. The reaction mixture is then distilled. 440 parts of N-diethylaminoacetonitrile (98% of theory) of boiling point 90° C/59 mm Hg are obtained; $n_D^{20} = 1.4260$.

EXAMPLE 4

Per hour, 796 parts of n-tridecylamine, 108 parts of hydrocyanic acid and 400 parts of a 30 percent strength by weight aqueous formaldehyde solution are introduced into a stirred kettle at 55° C, using the method described in Example 1, the hydrocyanic acid concentration being kept below 0.1 percent by weight, based on the total mixture. On average, the hydrocyanic acid concentration is from 0.08 to 0.09 percent by weight. Per hour, 1,304 parts of reaction mixture are obtained; the mixture separates into two phases. Using the method described in Example 1, 945 parts (99% of theory) of N-n-tridecylglycinonitrile are obtained as a pale yellowish oil; $n_D^{20} = 1.4565$.

EXAMPLE 5

1,135 parts of oleylamine are reacted using the method of Example 4. 1,264 parts of N-oleylglycinonitrile are obtained as a yellow oil; $n_D^{20} = 1.4669$.

We claim:
1. A process for the manufacture of an N-alkylglycinonitrile of the formula

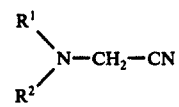

where $R^1$ and $R^2$ may be identical or different and each is alkyl of 1 to 20 carbon atoms or alkenyl of 2 to 20 carbon atoms, and $R^2$ may also be hydrogen, which process comprises: reacting an N-alkylamine of the formula

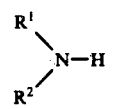

where $R^1$ and $R^2$ have the above meanings, with formaldehyde and hydrocyanic acid in the presence of water for from 0.1 to 4 hours and at a temperature of from above 40° up to 80° C., the concentration of the hydrocyanic acid during the reaction being not more than 0.1 percent by weight, based on the reaction mixture.

2. A process as claimed in claim 1, wherein the reaction is carried out with from 0.1 to 2 moles of amine per mole of formaldehyde, taken as 100% strength.

3. A process as claimed in claim 1, wherein the reaction is carried out at from 45° to 75° C.

4. A process as claimed in claim 1, wherein the reaction is carried out at from 50° to 70° C.

5. A process as claimed in claim 1, wherein the reaction is carried out with a total amount of from 1 to 6 moles of water per mole of formaldehyde.

6. A process as claimed in claim 1, wherein the reaction is carried out under conditions such that the concentration of hydrocyanic acid during the reaction is from 0.01 to 0.1 percent by weight, based on the reaction mixture.

7. A process as claimed in claim 1, wherein the reaction is carried out under conditions such that the concentration of hydrocyanic acid during the reaction is from 0.05 to 0.1 percent by weight, based on the reaction mixture.

8. A process as claimed in claim 1, wherein the reaction time is from 1 to 2 hours.

9. A process as claimed in claim 1, wherein the reaction is carried out in the presence of from 40 to 10,000 percent by weight, based on starting material II, of organic solvents which are inert under the reaction conditions.

* * * * *